(12) United States Patent
McParland

(10) Patent No.: US 8,785,869 B2
(45) Date of Patent: Jul. 22, 2014

(54) SYSTEM AND METHOD FOR PROVIDING EMISSION MAMMOGRAPHY

(75) Inventor: Brian James McParland, Amersham (GB)

(73) Assignee: General Electric Company, Schenectady, NY (US)

(*) Notice: Subject to any disclaimer, the term of this patent is extended or adjusted under 35 U.S.C. 154(b) by 419 days.

(21) Appl. No.: 11/264,454

(22) Filed: Nov. 1, 2005

(65) Prior Publication Data

US 2007/0096027 A1 May 3, 2007

(51) Int. Cl.
*G01T 1/00* (2006.01)
*G01T 1/166* (2006.01)

(52) U.S. Cl.
USPC ............. 250/370.09; 250/370.08; 378/37; 378/21; 600/407

(58) Field of Classification Search
USPC ......... 378/37, 21; 250/363.02, 363.03, 252.1, 250/363.01–363.09; 600/431, 436, 407, 600/425
See application file for complete search history.

(56) References Cited

U.S. PATENT DOCUMENTS

| | | | | |
|---|---|---|---|---|
| 4,485,819 A | * | 12/1984 | Igl | 600/445 |
| 5,252,830 A | * | 10/1993 | Weinberg | 250/363.02 |
| 5,519,221 A | * | 5/1996 | Weinberg | 250/363.02 |
| 6,201,247 B1 | * | 3/2001 | Lutheran et al. | 250/363.04 |
| 6,339,652 B1 | * | 1/2002 | Hawkins et al. | 382/131 |
| 6,377,838 B1 | * | 4/2002 | Iwanczyk et al. | 600/425 |
| 6,380,540 B1 | * | 4/2002 | Maor et al. | 250/363.04 |
| 6,399,951 B1 | * | 6/2002 | Paulus et al. | 250/370.13 |
| 7,038,210 B2 | * | 5/2006 | Tanaka et al. | 250/363.03 |
| 2004/0030246 A1 | * | 2/2004 | Townsend et al. | 600/427 |
| 2004/0183022 A1 | * | 9/2004 | Weinberg | 250/363.02 |
| 2004/0202280 A1 | * | 10/2004 | Besson | 378/37 |
| 2007/0023669 A1 | * | 2/2007 | Hefetz et al. | 250/370.14 |

OTHER PUBLICATIONS

Madore, Level 5: A Knowledgebase for Extragalactic Astronomy and Cosmology: "Flux", Retrieved from internet [Sep. 13, 2010]; Retrieved from url: <http://nedwww.ipac.caltech.level5/Glossary/Glossary_F.html>>; published Dec. 8, 2000.*
Macey et al., "Absolute Quantitiation of Radiotracer Uptake in the Lungs Using a Gamma Camera," Technical Notes, J. Nucl. Med. 23:731-735; 1982. Retrieved from internet [Sep. 12, 2010] Retrieved from url: <<http://jnm.snmjournals.org/cgi/reprint/23/8/731.pdf>>.*
E. Bombardieri et al., Breast Scintigraphy: procedure guidelines for tumour imaging, Eur J Nucl Med 30, 2003.
McParland, BJ et al., "A comparison of fixed and variable kVp technique protocols for film-screen mammography", Br J Radiol 73: 613-626, 2000.
Siegel et al., MIRD Pamphlet No. 16: Tech for quantitative radiopharm blodistr data acquisition and analysis for use in human rad dose estimates, J Nuc Med 40: 37S-61S, 1999.
Taillefer et al., Radionuclide Imaging of the Breast, New York: Marcel Dekker, Inc., 1998.

* cited by examiner

*Primary Examiner* — David Porta
*Assistant Examiner* — Yara B Green
(74) *Attorney, Agent, or Firm* — The Small Patent Law Group; Dean D. Small

(57) ABSTRACT

A system and method for providing emission mammography are provided. The system includes a first gamma emission detector and a second gamma emission detector. The first and second gamma emission detectors are configured to compress an object therebetween. The system further includes a radioactive transmission source. At least one of the first and second gamma emission detectors is configured to detect gamma ray photons from the radioactive transmission source.

27 Claims, 4 Drawing Sheets

SYSTEM AND METHOD FOR PROVIDING EMISSION MAMMOGRAPHY

BACKGROUND OF THE INVENTION

This invention relates generally to medical imaging systems, and more particularly, to emission mammography systems.

Imaging devices, such as gamma cameras or positron emission tomography scanners, are used in the medical field to detect radioactive emission events emanating from an object and to detect transmission or gamma rays attenuated by the object. An output, typically in the form of an image that graphically illustrates the distribution of the emissions within the object and/or the distribution of attenuation of the object is formed from these detections. The detector of an imaging device detects the number of emissions, for example, gamma rays in the range of about seventy keV to about six hundred keV, and may detect gamma rays that have passed through the object.

For example, single photon emitting-radionuclides, such as 99mTc, emit one gamma ray in a radioactive transition. These gamma rays are detected (typically by a scintillation detector, such as thallium-activated sodium iodide, NaI(Tl)) and are used to generate an image of the spatial distribution of the radionuclide. In addition, positron emission imaging generates images that represent the distribution of positron-emitting nuclides within the body of a patient. When a positron interacts with an electron by annihilation, the entire mass of a positron-electron pair is converted into two 511-keV photons. The photons are emitted in opposite directions along a line of response. The annihilation photons are detected by detectors that are placed on both sides of the line of response. When these photons arrive and are detected by the detector elements within a preset time interval, this is referred to as a true coincident event. An image is then generated based on the acquired image data that includes the annihilation photon detection information.

Different systems and methods for performing mammography imaging are known. For example, it is known to use x-ray systems for film screen mammography imaging. This type of mammography uses transmitted x-rays to produce an image of the breast. This type of mammography results in an image that represents the spatial distribution of the x-ray differential attenuation throughout the breast. This type of mammography imaging may not perform satisfactory imaging in women with dense breasts and further may not be able to provide sufficient differentiation to distinguish between benign and malignant lesions.

It is also known to perform Positron Emission Mammography (PEM) wherein radioactively tagged molecules (e.g., $^{18}$F-FDG) are injected into a patient to be imaged to mark or make more visible tissue that is more likely to be cancerous. Tumor cells show up as hot spots in the PEM images. It is also known to use single photon-emitting isotopes (such as $^{99m}$Tc) to perform scintimammography. Gamma cameras are thereby used to provide scintigraphic imaging wherein a radioactive tracer is employed and injected into a vein to identify abnormal cells based on the difference in physiological characteristics between cancer cells and non-cancer cells. The gamma camera is used to localize the radioactive tracer in the breast. Essentially, a gamma camera is placed at one or both sides of the breast to provide imaging of radiotracer distribution in the breast. Scintimammographic imaging systems also may use different types of detectors, such as, for example, cadmium zinc telluride (CZT) detectors.

Thus, emission mammography is typically performed using a conventional gamma camera, often referred to as scintimammography, with the patient either prone and the breast dependent or in lateral recumbence with the homolateral arm raised. Additionally, a gamma camera with a single detector can be used to emulate the positioning of a conventional x-ray mammography unit for nuclear medicine based studies. However, all of these known systems provide imaging of the breast in only a single view. Thus, quantitative measurement of in vivo activity contained within, for example, a tumor, cannot be reasonably or accurately obtained from single planar views because the thickness of both the overlying anatomy and the tumor are unknown.

BRIEF DESCRIPTION OF THE INVENTION

In an exemplary embodiment, a medical imaging system is provided that includes a first gamma detector and a second gamma detector. The first and second gamma emission detectors are configured to compress an object therebetween. The medical imaging system further includes a radioactive transmission source. At least one of the first and second gamma detectors is configured to detect gamma ray photons from the radioactive transmission source.

In an exemplary embodiment, a quantitative emission mammography conjugate-view imaging system is provided that includes a first gamma detector and a second gamma detector. The first gamma detector is variably positionable to compress a breast between the first gamma detector and the second gamma detector. Both detectors detect gamma rays emitted from the breast. The quantitative emission mammography conjugate-view imaging system further includes a radioactive transmission source. At least one of the first or second gamma detectors are configured to detect gamma ray photons from the radioactive transmission source.

In yet another exemplary embodiment, a method of performing a mammography is provided. The method includes compressing a breast between a pair of gamma detectors. The method further includes configuring at least one of the gamma detectors to detect gamma ray photons from a radioactive transmission source. The method also includes performing an imaging scan of a breast compressed between the pair of gamma detectors.

DETAILED DESCRIPTION OF THE INVENTION

Various embodiments of the invention provide a system and method for performing quantitative emission mammography (QEM). A technical effect of the various embodiments is to provide data indicative of underlying pathology, metabolism, progression or response to therapy relating to a tumor or lesion.

Figure 1:
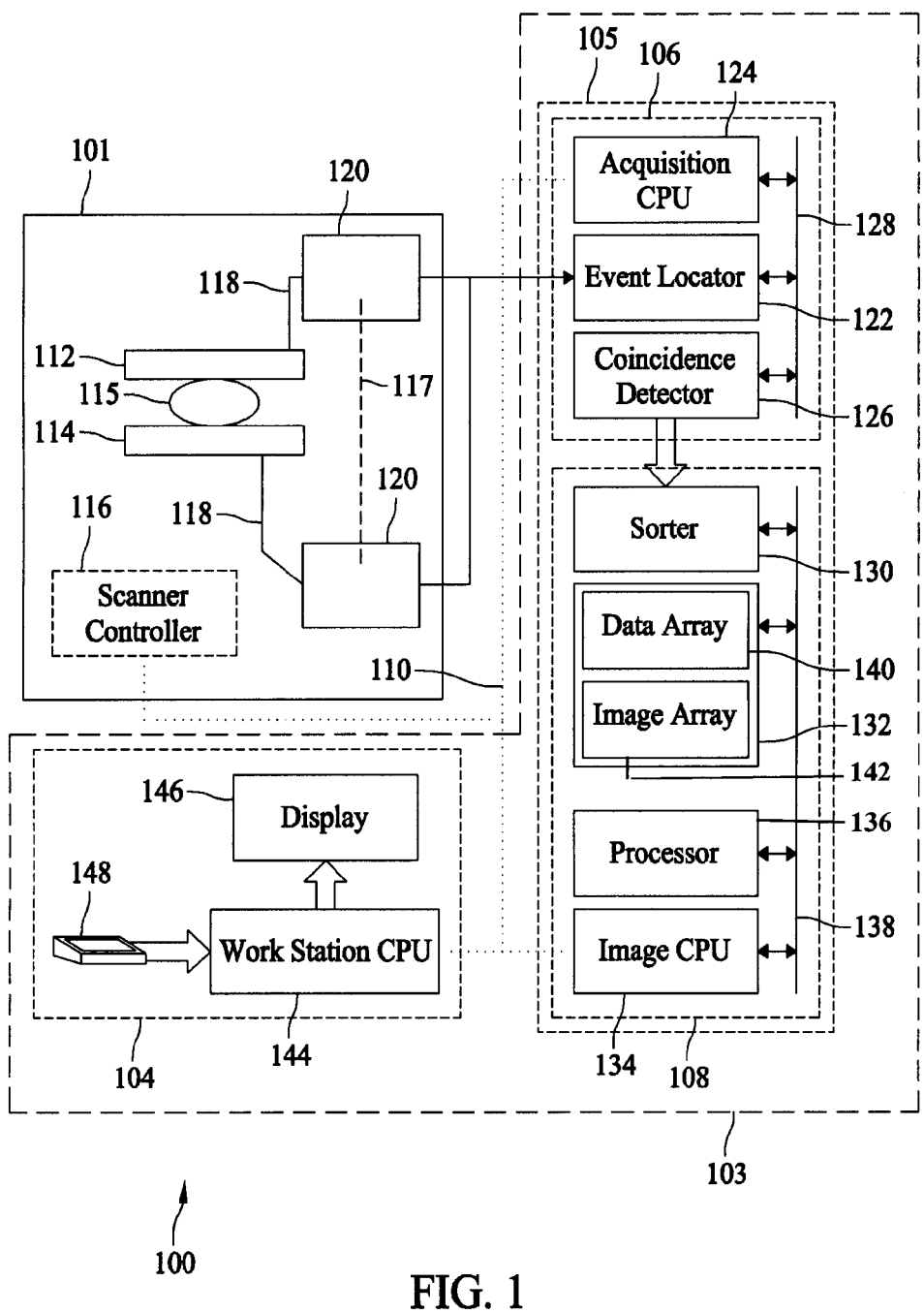
FIG. 1 is a block diagram of a quantitative emission mammography (QEM) system constructed in accordance with various exemplary embodiments of the invention.

FIG. 1 is a block diagram of a QEM system 100 constructed in accordance with various embodiments of the invention. The QEM system 100 includes a QEM scanner 101 and a controller 103 to control image reconstruction processes. The controller 103 includes an operator workstation 104, and a processor 105. The processor 105 includes a data acquisition processor 106 and an image reconstruction processor 108. The QEM scanner 101, operator workstation 104, data acquisition processor 106 and image reconstruction processor 108 are interconnected via a communication link 110 (e.g., a serial communication or wireless link). The QEM scanner 101, which in various embodiments includes a gantry (not shown) configured for rotation, acquires scan data and transmits the data to the data acquisition processor 106. The operation of the QEM scanner 101 is controlled from the operator workstation 104. The data acquired by the data acquisition processor 106 is reconstructed using a reconstruction processor 108.

In various embodiments, the QEM scanner 101 operates using a plurality of gamma cameras or detectors. In particular, the QEM scanner 101 includes a first detector 112 (e.g., a superior detector) and a second detector 114 (e.g., an inferior detector). At least one of the detectors 112 and 114 is moveable for positioning therebetween an object, such as a human breast 115. The detectors 112 and 114 may be moved into position by motors on the gantry. A QEM scanner controller 116, also referred to as a gantry controller, is provided (e.g., mounted) within the QEM scanner 101. The QEM scanner controller 116 responds to commands received from the operator workstation 104 through the communication link 110. Therefore, the operation of the QEM scanner 101 is controlled from the operator workstation 104 through the QEM scanner controller 116.

Each of the detectors 112 and 114 may include a plurality of detector elements, for example, one or more scintillator crystals (or semiconductor detectors) arranged in a matrix that are disposed in front of a plurality of photomultiplier tubes (e.g., four tubes). When a photon collides with a crystal on a detector, the photon produces a scintilla in the crystal. Each photomultiplier tube produces an analog signal on the communication line 118 when a scintillation event occurs. A set of acquisition circuits 120 is provided within the QEM scanner 101 to receive the analog signals. The acquisition circuits 120 produce digital signals indicating the two-dimensional (2D) location and total energy of the event. The acquisition circuits 120 also produce an event detection pulse, which indicates the time or moment the scintillation event occurred. This is only needed for coincidence detection of photon pairs resulting from using a positron-emitting tracer. These digital signals are transmitted through a communication link, for example, a cable, to an event locator circuit 122 in the data acquisition processor 106.

The data acquisition processor 106 includes the event locator 122, an acquisition CPU 124 and, only in the event of the use of a positron-emitting tracer, a coincidence detector 126. The data acquisition processor 106 periodically samples the signals produced by the acquisition circuits 120. The acquisition CPU 124 controls communications on a back-plane bus 128 and on the communication link 110. The event locator circuit 122 processes the information regarding each valid event and provides a set of digital numbers or values indicative of the detected event. For example, this information could indicate when the event took place and the position within the scintillation crystal that detected the event. For single-photon emitting radioisotopes, such as $^{99m}$Tc, such information is generally sufficient. However, additional information may be needed. In such a case, an event data packet is communicated to the coincidence detector 126 through the back-plane bus 128. The coincidence detector 126 receives the event data packets from the event locator circuit 122 and determines if any two of the detected events are in coincidence. Coincidence is determined by a number of factors. First, the time markers in each event data packet must be within a predetermined time period, for example, 12.5 nanoseconds, of each other. Second, the LOR formed by a straight line joining the two detectors 112 and 114 that detect the coincidence event should pass through the field of view in the QEM scanner 101. Events that cannot be paired are discarded. Coincident event pairs are located and recorded as a coincidence data packet that is communicated through a communication link to a sorter 130 in the image reconstruction processor 108.

The Image reconstruction processor 108 includes the sorter 130, a memory module 132, an image CPU 134, an array processor 136 and a back-plane bus 138. The data array 140 is stored in the memory module 132. The back-plane bus 138 is linked to the communication link 110 through the image CPU 134. The image CPU 134 controls communication through the back-plane bus 138. The array processor 136 is also connected to back-plane bus 138. The array processor 136 receives the data array 140 as an input and reconstructs images in the form of image arrays 142. The resulting image arrays 142 are stored in the memory module 132.

The images stored in the memory module 132 are communicated by the image CPU 134 to the operator workstation 104. The operator workstation 104 includes a CPU 144, a display device 146 and an input device 148. The CPU 144 is connected to communication link 110 and receives inputs (e.g., user commands) from the input device 148. The input device 148 may be, for example, a keyboard, mouse, or a touch-screen panel. Through the input device 148 and associated control panel switches, the operator can control the calibration of the QEM scanner 101, the configuration of the QEM scanner 101, and the positioning of the detectors 112 and 114 for a scan. The input device 148 can also control the processing performed by the image CPU 134 by specifying, for example, the filters and processing methods used in the reconstruction. Similarly, the operator can control the display of the resulting image on the display device 146 and perform image-enhancement functions using programs executed by the workstation CPU 144.

The Processor 105 is configured to process the scan information received from the detectors 112 and 114. The scan information can include, for example, image and timing information that is received by the processor 105 from the detectors 112 and 114 during an imaging scan. The timing information in one embodiment is the difference in time at which two photons emitted in a photon event are detected by the detectors 112 and 114. The timing information may include time stamp information relating to a measured photon event detected by a pair of elements in the detector elements 112 and 114 for the QEM system 100. The time stamp information is the time at which each photon is detected by the detectors 112 and 114.

Figure 2:
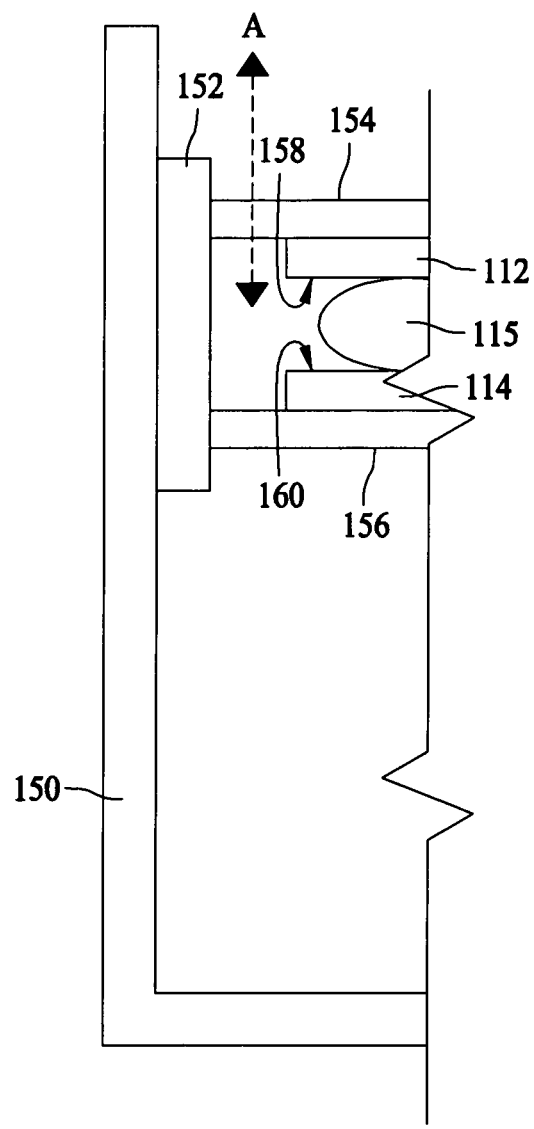
FIG. 2 is a side elevation view of a QEM scanner constructed in accordance with an exemplary embodiment of the invention.

In various exemplary embodiments, and as shown in FIG. 2, the QEM scanner 101 (shown in FIG. 1) includes the two detectors 112 and 114, which are two gamma camera emission detectors or gamma ray photon detectors, each optionally having a substantially rectangular polyhedrally shaped body. The detectors 112 and 114 are mounted on or otherwise coupled to a detector support 150. The detector support 150 may be configured as a stand-alone unit, a moveable transport unit, etc. More particularly, the detector support 150 includes a gantry 152 configured for rotation as described in more detail herein. The gantry 152 includes a first detector support 154 configured to support the first detector 112 and a second detector support 156 configured to support the second detector 114. In an exemplary embodiment, the first detector support 154 is configured for variable positioning, for example, is configured for translation relative to the gantry 152 as indicated by the arrow A. In this exemplary embodiment, the second detector support 156 is fixed on the gantry 152. The gantry 152 with the first detector support 154 and the second detector support 156 may form a C-arm configuration.

The first detector support 154 and the second detector support 156 are configured such that a detecting face 158 of the first detector 112 and a detecting face 160 of the second detector 114 are oriented substantially parallel with respect to each other (i.e., the detectors 112 and 114 are positioned 180 degrees apart). Generally, both of the detectors 112 and 114 are oriented such that a normal centerline of the detecting faces 158 and 160 are oriented substantially orthogonally to an examination axis, thereby providing a conjugate view arrangement for imaging. In operation, each of the detectors 112 and 114 may be controlled separately and may activated at different times.

It should be noted that the detectors 112 and 114 may be constructed or formed of different materials. The detectors 112 and 114 may include radiation detectors constructed from, for example, scintillation materials such as sodium iodide or caesium iodide with associated photomultiplier tubes or other photo-detectors such as solid state photodiodes, radiation-sensitive scintillation material and a light detecting device, or may be fabricated from a semiconductor radiation detector including, for example, but not limited to, cadmium zinc telluride (CZT). For example, any conventional scintigraphic detection modality material may be used. However, it should be noted that the use of NaI scintillation crystals requires physical collimation. In various embodiments, high-density/high atomic number pixellated solid-state detectors with a high conversion efficiency are provided. For example, a 5120-pixel device with a 16×20 cm² field-of-view using cadmium zinc telluride (CdZTe) may be incorporated into a single detector imaging unit. Other possible materials include, for example, GaAs. These detectors may be provided using detector units, as are known.

In various exemplary embodiments, both of the detectors 112 and 114 are used for emission imaging, and in particular, gamma photon ray emission imaging. For example, a breast 115 is positioned on top of the second detector 114 and the first detector 112, mounted on the variably-positionable first detector support 154, is moved (e.g., translated) to contact the breast 115. Slight compression by the first detector 112 is normally provided. The gantry 152 also allows rotation of the detectors 112 and 114, while still retaining the first and second detectors 112 and 114 in a parallel-opposed orientation, for example, a forty-five degree rotation in order to provide medio-lateral views in addition to cranio-caudad views of the breast 115.

In operation, to determine in vivo activity from conjugate-view view imaging, the activity within a lesion or tumor of thickness t in the breast 115 imaged by the two conjugate detectors 112 and 114, which also may be referred to as the superior detector and inferior detector, respectively, is defined by the following equation:

$$A = \frac{\sqrt{C_S C_I}}{T_\chi \sqrt{\Im} \left( \frac{\sinh\left(\frac{\mu t}{2}\right)}{\left(\frac{\mu t}{2}\right)} \right)} \quad (1)$$

where $C_S$ and $C_I$ are the measured counts from each detector over the time interval T, $\chi$ is the calibration factor converting from the measured count rate to activity measured in air (in units of, for example, $$\frac{cpm}{MBq})$$

and $\Im$ is the measured fraction of photons transmitted through the imaged breast region containing the lesion. The following factor accounts for photon self-attenuation within the lesion itself:

$$\frac{\sinh\frac{\mu t}{2}}{\left(\frac{\mu t}{2}\right)} \quad (2)$$

where $\mu$ is the linear attenuation coefficient in breast tissue for the photon energy of interest. The factor (2) is often negligibly different from unity. For the example of a one cm thick lesion being imaged with $^{99m}Tc$ where $\mu=0.12$ cm$^{-1}$, $$\frac{\sinh\frac{\mu t}{2}}{\left(\frac{\mu t}{2}\right)}$$

differs from unity by less than 0.06%. Hence, the factor (2) may be omitted from Equation 1 to yield the following equation:

$$A = \frac{\sqrt{C_S C_I}}{T_\chi \sqrt{\Im}} \quad (3)$$

It should be noted that in the conjugate-view imaging process, no knowledge of the physical depth of the lesion in tissue is needed (i.e., no t dependence in Equations 1 and 3). The overall thickness of the anatomy does need to be known implicitly, however the thickness is given by a measurement of $\Im$.

Figure 3:
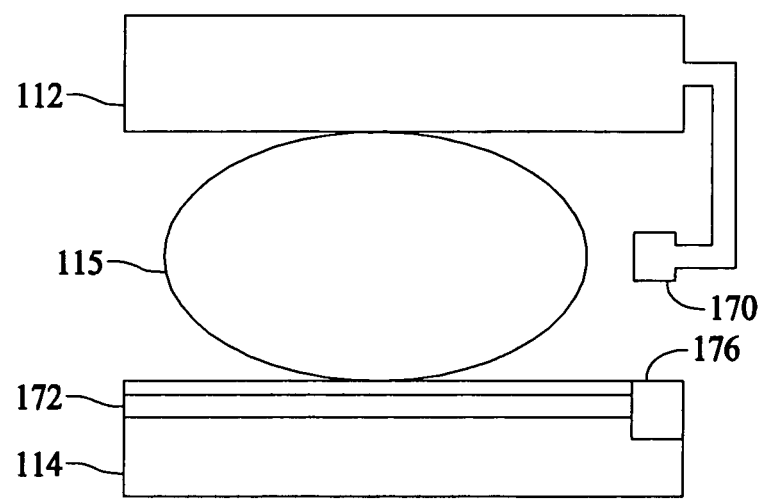
FIG. 3 is a side elevation view of a QEM scanner constructed in accordance with another exemplary embodiment of the invention showing a calibration source.

In an exemplary embodiment as shown in FIG. 3, the detectors 112 and 114 and configured for imaging in connection with a transmission source 172, and optionally a calibration source 170. More particularly, the calibration source 170 contains a known amount of radioactivity (of the same isotope used in a radiopharmaceutical injected into a patient). The calibration source is positioned generally equidistant or midway between the two detectors 112 and 114. Measurement of the count rate geometric mean from the calibration source 170 establishes the calibration factor, $\chi$ of Equation 1 above. It should be noted that if the energy and count rate responses of the detectors 112 and 114 are known and are stable, calibration may be separately performed (not concurrently with imaging the source).

The transmission, $\Im$, is a required factor in evaluating the in vivo activity. This is determined by measuring the intensity of gamma ray photons from an external source, such as the transmission source 172, as the gamma ray photons are attenuated by the breast 115 and internal anatomy, including, for example, a lesion. In one exemplary embodiment, the transmission source 172 is a line source containing, for example, $^{57}$Co or $^{153}$Gd placed inside the structure of the second detector 114, immediately above the active detection area. In operation, the transmission source 172 is translated across the detecting face 158 of the second detector 114, for example, by a motor-drive (not shown). It should be noted that a shielded receptacle 176, for example, a lead shielded receptacle, also is provided for storing the transmission source 172, and in particular, the line source, during imaging.

In another embodiment, a slot (not shown) may be provided in the structure of the second detector 114, also immediately above the active detection area. A user can insert, for example, a $^{57}$Co flood source into the slot for the transmission measurement.

It should be noted that different collimator arrangements may be provided. For example, collimators may be provided on the detectors 112 and 114. Additionally or alternatively, collimators may be provided on the detectors 112 and 114 and the transmission source 172.

Figure 4:
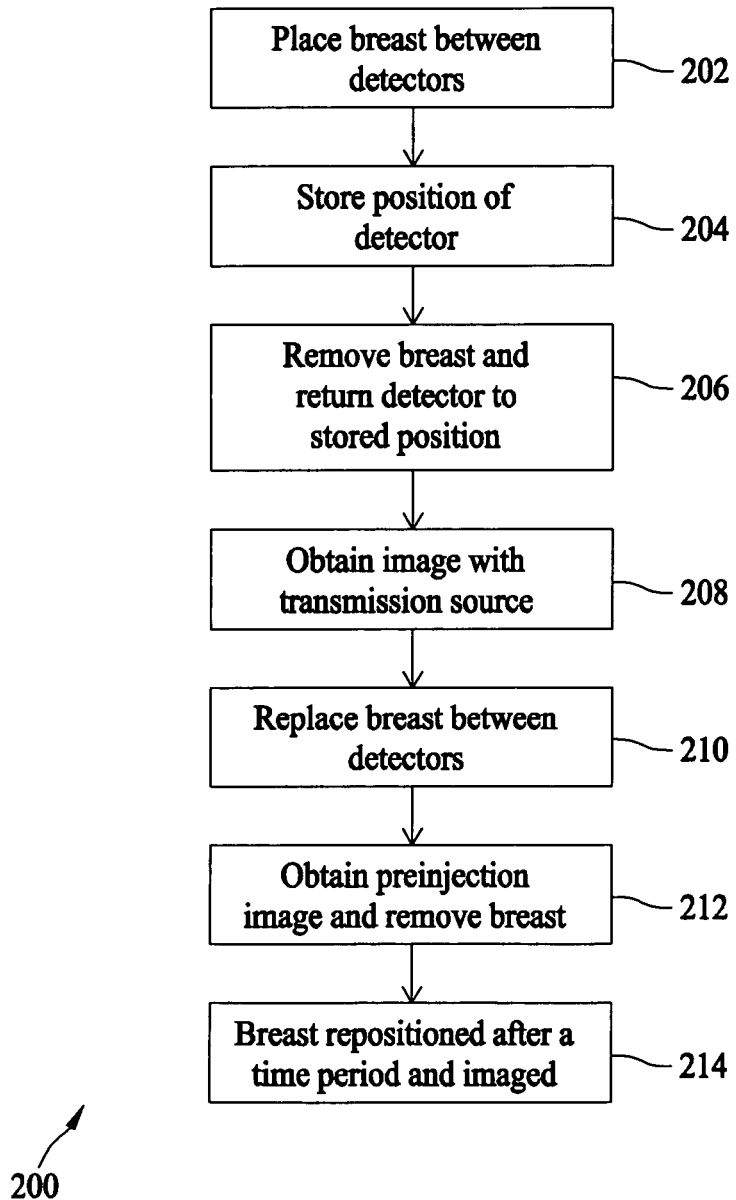
FIG. 4 is a flowchart of a method for performing quantitative imaging in accordance with various embodiments of the invention.

In various embodiments, imaging using the QEM system 100 (shown in FIG. 1) is provided by a method 200, shown in FIG. 4, that includes first performing a transmission measurement, which may include an attenuation scan, followed by performing quantitative imaging. Reference is also made to FIGS. 1 through 3. In particular, it is assumed that the sensitivity of the first detector 112 varies with position from the breast 115. Prior to injection of the radiopharmaceutical, at 202, the breast 115 is placed and aligned with the detectors 112 and 114 and the first detector 112 lowered to the correct contact and compression position, for example, based on predetermined criteria or as is known in the art. This position is then stored at 204, for example in a memory of the QEM system 100. This stored position information may be used to provide reproducibility. At 206, the first detector 112 is released (e.g., translated away from the breast 115), the breast 115 removed and the first detector 112 returned to the original contact position. The positioning of the detector 112 is performed electronically using, for example, the scanner controller 116 (shown in FIG. 1).

At 208, the transmission source 172 is then translated (if an internal line source) or inserted (if an external flood source) and an image (without any absorbing tissue) acquired with the first detector 112. Thereafter at 210, the first detector 112 is released, the breast 115 repositioned and the first detector 112 returned to the stored contact position. A pre-injection image is then acquired at 212 by the first detector 112 with the transmission source 172, for example, the translatable internal source or the insertable external source. From the two acquired image data sets, a pixel-by-pixel evaluation of the transmission is then calculated. In particular, attenuation by the breast 115 is calculated. The breast 115 is then removed. It should be noted that in various embodiments, a compression plate may be used during a portion of the transmission measurement process.

At an appropriate time following administration of the radiopharmaceutical to a patient, as is known in the art, at 214, the breast 115 is repositioned and the first detector 112 returned to the contact position, without the transmission source 170 present, for example, with the transmission source 170 stored in the slot. The breast 115 (and optionally the calibration source 170) are then imaged by both the first and second detectors 112 and 114.

Once the breast 115 is positioned appropriately and imaged post-injection, images from the superior and inferior views are acquired. Off-line regions-of-interest may be drawn about the lesion and a nearby background area to exclude contributions from the background.

It should be noted that the imaging method 200 may be repeated with the detectors 112 and 114 rotated ninety degrees. For example, a superior to inferior imaging process is first performed, the breast removed, and then a medial to lateral imaging process is performed. Thus, medio-lateral views in addition to cranio-caudad views of the breast 115 may be generated.

Thus, a QEM system is provided, for example, configured as an upright dual-detector conjugate-view unit that reproduces the positioning capabilities of a conventional x-ray mammography unit and in which the imaged breast is intermediate to the two detectors. Conventional mammographic views (e.g., cranio-caudad and medio-lateral) can be obtained by this QEM system. Different embodiments may be provided having a removable or translatable radioactive flood source for transmission measurements and a radioactive calibration source of known activity to allow quantitative measurements of the distribution of activity within the breast.

The various embodiments or components, for example, of the QEM system 100 and components or controllers therein, may be implemented as part of one or more computer systems, which may be separate from or integrated with the QEM system 100. The computer system may include a computer, an input device, a display unit and an interface, for example, for accessing the Internet. The computer may include a microprocessor. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device may also be other similar means for loading computer programs or other instructions into the computer system.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer system executes a set of instructions that are stored in one or more storage elements, in order to process input data. The storage elements may also store data or other information as desired or needed. The storage element may be in the form of an information source or a physical memory element within the processing machine.

The set of instructions may include various commands that instruct the computer as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While the invention has been described in terms of various specific embodiments, those skilled in the art will recognize that the invention can be practiced with modification within the spirit and scope of the claims.

What is claimed is:

1. A medical imaging system comprising:
   a first cadmium zinc telluride (CZT) gamma detector;
   a second CZT gamma detector, the first and second CZT gamma detectors configured to compress an object therebetween to immobilize the object and detect emission photons; and
   a gantry configured for rotation, the gantry further configured to support the first CZT gamma detector, the second CZT gamma detector and a transmission source, the gantry providing variable positioning of the first CZT gamma detector, wherein the first CZT gamma detector is coupled to the gantry and configured for movement along the gantry and the second CZT gamma detector is fixedly held to the gantry.

2. A medical imaging system in accordance with claim 1 wherein the transmission source comprises a line source.

3. A medical imaging system in accordance with claim 1 wherein the transmission source is a line source that is translatable across a face of one of the first gamma detector and second gamma detector.

4. A medical imaging system in accordance with claim 1 wherein the transmission source is a flood source.

5. A medical imaging system in accordance with claim 1 further comprising a receptacle configured to store the transmission source therein.

6. A medical imaging system in accordance with claim 1 further comprising a calibration source.

7. A medical imaging system in accordance with claim 1 wherein the gantry is configured to rotate to provide mediolateral and cranio-caudad imaging.

8. A medical imaging system in accordance with claim 1 wherein the first and second gamma detectors comprise gamma cameras.

9. A medical imaging system in accordance with claim 1 wherein the object is a human breast and the first and second gamma detectors are configured to provide mammography imaging.

10. A medical imaging system in accordance with claim 1 further comprising a memory and wherein a compression position of the first gamma detector is stored in the memory.

11. A medical imaging system in accordance with claim 1 wherein each of the first CZT gamma detector and the second CZT gamma detector having a substantially rectangular polyhedrally shaped body.

12. A medical imaging system in accordance with claim 1 wherein the emission photons comprise one of photon pairs for positron emission tomography (PET) imaging and single photons for single photon emission computed tomography (SPECT) imaging.

13. A medical imaging system in accordance with claim 1 wherein the first and second CZT gamma detectors are configured to compress the object therebetween without a compression plate.

14. A medical imaging system in accordance with claim 1 wherein the second CZT gamma detector is not capable of movement with respect to the first CZT gamma detector.

15. A medical imaging system in accordance with claim 1 wherein the second CZT gamma detector is not capable of translating along the gantry towards or away from the first CZT gamma detector.

16. A quantitative emission mammography conjugate-view imaging system comprising:
    a first gamma detector coupled to a gantry and configured for movement along the gantry;
    a second gamma detector fixedly held to the gantry, the first gamma camera variably positionable with the movement to compress a breast between the first gamma detector and the second gamma detector to immobilize the breast therebetween;
    a translatable radioactive transmission source, at least one of the first and second gamma detectors configured to detect gamma ray photons from the radioactive transmission source;
    a shielded receptacle for storing the translatable radioactive transmission source; and
    a calibration source coupled generally along an end of a field of view of the first and second gamma cameras.

17. A quantitative emission mammography conjugate-view imaging system in accordance with claim 16 wherein the transmission source is one of a line source and a flood source.

18. A quantitative emission mammography conjugate-view imaging system in accordance with claim 16 wherein the first and second gamma detectors comprise solid-state detectors.

19. A method for performing diagnostic imaging, the method comprising:
    detecting emission photons utilizing a first cadmium zinc telluride (CZT) gamma detector and a second CZT gamma detector, the first and second CZT gamma detectors configured to compress an object therebetween to immobilize the object, wherein the first CZT detector is movable relative to a gantry and the second CZT gamma detector is fixedly held to the gantry; and
    detecting transmission photons from a radioactive transmission source utilizing the first and second CZT gamma detectors.

20. A method in accordance with claim 19 further comprising translating the radioactive transmission source.

21. A method in accordance with claim 19 further comprising configuring a gantry for rotation and to support the first CZT gamma detector, the second CZT gamma detector and the transmission source, the gantry providing variable positioning of the first CZT gamma detector.

22. A quantitative emission mammography conjugate-view imaging system comprising:
    a first gamma camera coupled to a gantry and configured for translation relative to the gantry;
    a second gamma camera fixedly held to the gantry, the first gamma camera variably positionable with the translation to compress a breast between the first gamma camera and the second gamma camera; and
    a processor, configured to receive a first emission image from the first gamma camera and a second emission image from the second gamma camera and calculate quantitative distribution of radiopharmaceutical isotope in the breast based on the received first and second images and the thickness of the lightly compressed breast.

23. A quantitative emission mammography system in accordance with claim 22 wherein the calculation of in vivo activity for a quantitative distribution A of radiopharmaceutical isotope in the breast comprises using the equation:

$$A=(C_1 * C_2)^{1/2}/(x*T*F^{1/2})$$

wherein, C1 and C2 are the photon counts in the first and second images respectively, x is a calibration factor converting from a measured count rate to activity measured in air, T is a photon acquisition time and F is a fraction of photons transmitted through the imaged breast region containing a lesion.

24. A quantitative emission mammography system in accordance with claim 23 further comprising a transmission source and wherein the fraction F of photons transmitted through the imaged breast region containing the lesion is measured using the transmission source.

25. A quantitative emission mammography system in accordance with claim 23 wherein the fraction F is calculated from the attenuation coefficient of the breast and the thickness of the lightly compressed breast.

26. A quantitative emission mammography system in accordance with claim 23 further comprising a calibration source and wherein the calibration factor x is measured using the calibration source.

27. A quantitative emission mammography system in accordance with claim 23 wherein the quantitative distribution of radiopharmaceutical isotope in the lesion is corrected for self absorption using the equation:

$$A'=A*(\operatorname{Sin} h[u*t/2])/(u*t/2)$$

wherein u is an attenuation coefficient of the breast and t is the thickness of a lesion within the breast.

* * * * *